US009285356B2

(12) United States Patent
Al-Jabari

(10) Patent No.: US 9,285,356 B2
(45) Date of Patent: Mar. 15, 2016

(54) DETERMINING OIL VISCOSITY BASED ON BIODEGRADATION

(71) Applicant: Halliburton Energy Services, Inc., Houston, TX (US)

(72) Inventor: Naim Wajih Al-Jabari, Abu Dhabi (AE)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/996,526

(22) PCT Filed: Sep. 25, 2012

(86) PCT No.: PCT/US2012/057088
§ 371 (c)(1),
(2) Date: Jun. 20, 2013

(87) PCT Pub. No.: WO2014/051546
PCT Pub. Date: Apr. 3, 2014

(65) Prior Publication Data
US 2015/0219613 A1    Aug. 6, 2015

(51) Int. Cl.
*G01N 33/28* (2006.01)
*C12Q 1/64* (2006.01)
*G01N 21/64* (2006.01)
*E21B 49/08* (2006.01)
(Continued)

(52) U.S. Cl.
CPC .............. *G01N 33/2823* (2013.01); *C12Q 1/64* (2013.01); *E21B 49/08* (2013.01); *G01N 11/00* (2013.01); *G01N 21/6402* (2013.01); *G01N 33/2835* (2013.01); *G01N 33/4833* (2013.01); *E21B 2049/085* (2013.01); *G01N 11/16* (2013.01)

(58) Field of Classification Search
CPC .... G01N 11/04; G01N 11/16; G01N 33/2829
USPC ......................................... 73/54.02; 166/246
See application file for complete search history.

(56) References Cited

U.S. PATENT DOCUMENTS 4,905,761 A * 3/1990 Bryant .......................... 166/246
5,529,930 A   6/1996 Monticello et al.
(Continued)

FOREIGN PATENT DOCUMENTS

WO    WO2009029502    3/2009

OTHER PUBLICATIONS

Carlson et al., "Viscosity Correlations Among Heavy Crude Oils of the San Joaquin Valle, California", No. 1998.203, 1998.*
(Continued)

*Primary Examiner* — Lisa Caputo
*Assistant Examiner* — Nathaniel T Woodward
(74) *Attorney, Agent, or Firm* — Scott H. Brown; Fish & Richardson P.C.

(57) ABSTRACT

Methods, computer-readable media, and systems for determining oil viscosity based on biodegradation are described. A chemical signature of oil obtained from a subterranean zone is received. An amount of bacteria associated with oil in the zone based on the chemical signature of the oil is received. Using an empirical relationship relating oil viscosities to amounts of bacteria, an oil viscosity that is empirically related to the amount of bacteria is identified. The identified oil viscosity for the oil is provided, for example, in response to input requesting oil viscosity.

19 Claims, 5 Drawing Sheets

(51) Int. Cl.
*G01N 11/00* (2006.01)
*G01N 33/483* (2006.01)
*G01N 11/16* (2006.01)

(56) References Cited

U.S. PATENT DOCUMENTS

| | | |
|---|---|---|
| 7,052,901 B2 | 5/2006 | Crews |
| 7,511,487 B2 | 3/2009 | Badry et al. |
| 7,511,488 B2 | 3/2009 | Romero et al. |
| 7,691,908 B2 | 4/2010 | Bokotko et al. |
| 7,718,956 B2 | 5/2010 | Ferguson |
| 7,728,291 B2 | 6/2010 | Bello |
| 7,776,795 B2 | 8/2010 | Keeler et al. |
| 7,804,296 B2 | 9/2010 | Flaum et al. |
| 7,965,078 B2 | 6/2011 | Cheng et al. |
| 8,013,601 B2 | 9/2011 | Cheng et al. |

OTHER PUBLICATIONS

Henshaw et al, "Evaluation of Geochemical Approaches to Heavy Oil Viscosity Mapping in San Joaquin Valley, California", SPE 46205, 1998.*

Authorized Officer in Ho Han, PCT International Preliminary Report on Patentability, PCT/US2012/057088, Apr. 26, 2015, 6 pages.

R.M.K. Carlson et al., "Geochemical—Viscosity Correlations Among Heavy Crude Oils of the San Joaquin Valley, California" Society of Petroleum Engineers, 1998 (24 pages).

Prof. Zhang Tingshan, "Microbial Degradation Influences on Heavy Oil Characters and MEOR Test" World Petroleum Congress, 2004 (7 pages).

Notification of Transmittal of the International Search Report and the Written Opinion of the International Searching Authority, or Declaration (2 pages); International Search Report (4 pages); and Written Opinion of the International Searching Authority (4 pages), mailed Apr. 26, 2013, for related international application PCT/US2012/057088.

Permanyer et al., "Cruide Oil Biodegradation and Environmental Factors at the Riutort Oil Shale Mine, Se Pyresees" Journal of Petroleum Geology, vol. 33, Issue 2, Mar. 26, 2010, pp. 123-139.

G.A. Plaza et al., "Biodegradation of Crude Oil and Distillation Products by Biosurfactant-Producing Bacteria" Polish J. of Environ. Stud. vol. 17, 2008, pp. 87-94.

G.J. Mulkins-Phillips et al., "Effect of Four Dispersants on Biodegradation and Growth of Bacteria on Crude Oil" Applied Microbiology, vol. 28, No. 4, Oct. 1974, pp. 547-552.

Wang, Q. et al., "Engineering Bacteria for Production of Rhamolipid as an Agent for Enhanced Oil Recovery", Biotechnoogy and Bioengineering, Nov. 1, 207, vol. 98, pp. 842-853—"see the whole document".

Minh, et al., "Evaluation of Congo Heavy Oil Reservoir with Novel NMR Logging", SPWLA 47th Annual Logging Symposium, Jun. 4-7, 2006, 8 pages.

Decoster, et al., "Application of Recent NMR Developments to the Characterization of Orinoco Belt Heavy Oil Reservoirs", SPWLA 49th Annual Logging Symposium, May 25-28, 2008, 16 pages.

Sun, et al., "Direct Fluid Typing and Quantification of Orinoco Belt Heavy Oil Reservoirs using 2D NMR Logs", SPWLA 47th Annual Logging Symposium, Jun. 4-7, 2006, 8 pages.

Bryan, et al., "In Situ Viscosity of Heavy Oil: Core and Log Calibrations", Journal of Canadian Petroleum Technology, Nov. 2007, vol. 46, No. 11, 9 pages.

Freedman, et al., "Fluid Characterization Using Nuclear Magnetic Resonance Logging", Petrophysics, vol. 45, No. 3, May-Jun. 2004, p. 241-250, 10 pages.

Chen, et al., "Application of NMR Logging for Characterizing Movable and Immovable Fractions of Viscose Oils in Kazakhstan heavy Oil Field", SPWLA 47th Annual Logging Symposium, Jun. 4-7, 2006, 12 pages.

Gushor Inc's Blog, "Heavy Oil Biodegradation—Important?", Posted Oct. 26, 2011, 4 pages.

Heavy Oil, "Geochemical Approaches to Heavy-Oil Viscosity Mapping", Synopsis of paper SPE 46205, Sep. 1998, JPT, 3 pages.

Idris, Kamil, "Vertical and Lateral Delineation of Tar and Heavy Oil Reservoirs; Practical Considerations for a Challenging Task—Towards Optimum and Improved Recovery", Reservoir Characterization Department, Saudi Aramco, Third EAGE/SPE Workshop on Tar Mats May 20-23, 2012, Abu Dhabi, UAE, 1 page.

Greater Insight for Wellbore Positioning and Formation Evaluation While Drilling, LaserStrat Chemostratigraphy, Hallliburton Website 2011, 8 pages.

GEM™ Elemental Analysis Tool, Precise Evaluation of Complex Mineralogies, Halliburton Website, 2009, 2 pages.

* cited by examiner

DETERMINING OIL VISCOSITY BASED ON BIODEGRADATION

TECHNICAL FIELD

This disclosure relates to oil, for example, heavy oil, in formations and wells.

BACKGROUND

Crude oil can be classified into light oil (for example, oil that has a low density, viscosity, and specific gravity, and can flow freely at room temperature) and heavy oil (for example, oil that has higher viscosity and specific gravity than light crude oil, and that cannot flow easily). A determination of the viscosity of oil can aid in the successful recovery of the oil from oil wells. For example, Nuclear Magnetic Resonance (NMR) techniques can be used to determine the viscosity of heavy oil.

Under certain conditions, the organisms, for example, bacteria, yeasts, molds, fungi, and the like, can form various classes of compounds present in oil by processes collectively termed as biodegradation. Such biodegradation can affect the properties, for example, viscosity, of the oil.

DESCRIPTION OF DRAWINGS

Like reference symbols in the various drawings indicate like elements.

DETAILED DESCRIPTION

This disclosure describes methods and systems for determining oil viscosity based on biodegradation. The formation of oil can be affected by several factors including pressure, temperature, bacteria, and the like. Of these factors, biodegradation due to bacteria (or combination of bacteria with other biological organisms) can play a dominant role in shallow subterranean formations or zones of interest. For example, biodegradation can increase oil viscosity in shallow oil zones such that oil with greater amounts of bacteria can have a greater viscosity. A zone of interest (henceforth "zone") can be a particular formation or can include multiple formations or can be a portion of a formation. Using the techniques described below, this effect of biodegradation on oil viscosity can be exploited to determine viscosities of oil obtained from a zone in multiple locations across multiple fields from which oil is to be produced. A three-dimensional map of viscosities developed using the determined viscosities, that is unique to the field, can be used to plan and develop the field, for example, to identify locations to drill wells, identify well completion procedures, identify surface installation equipment, and the like.

Figure 1:
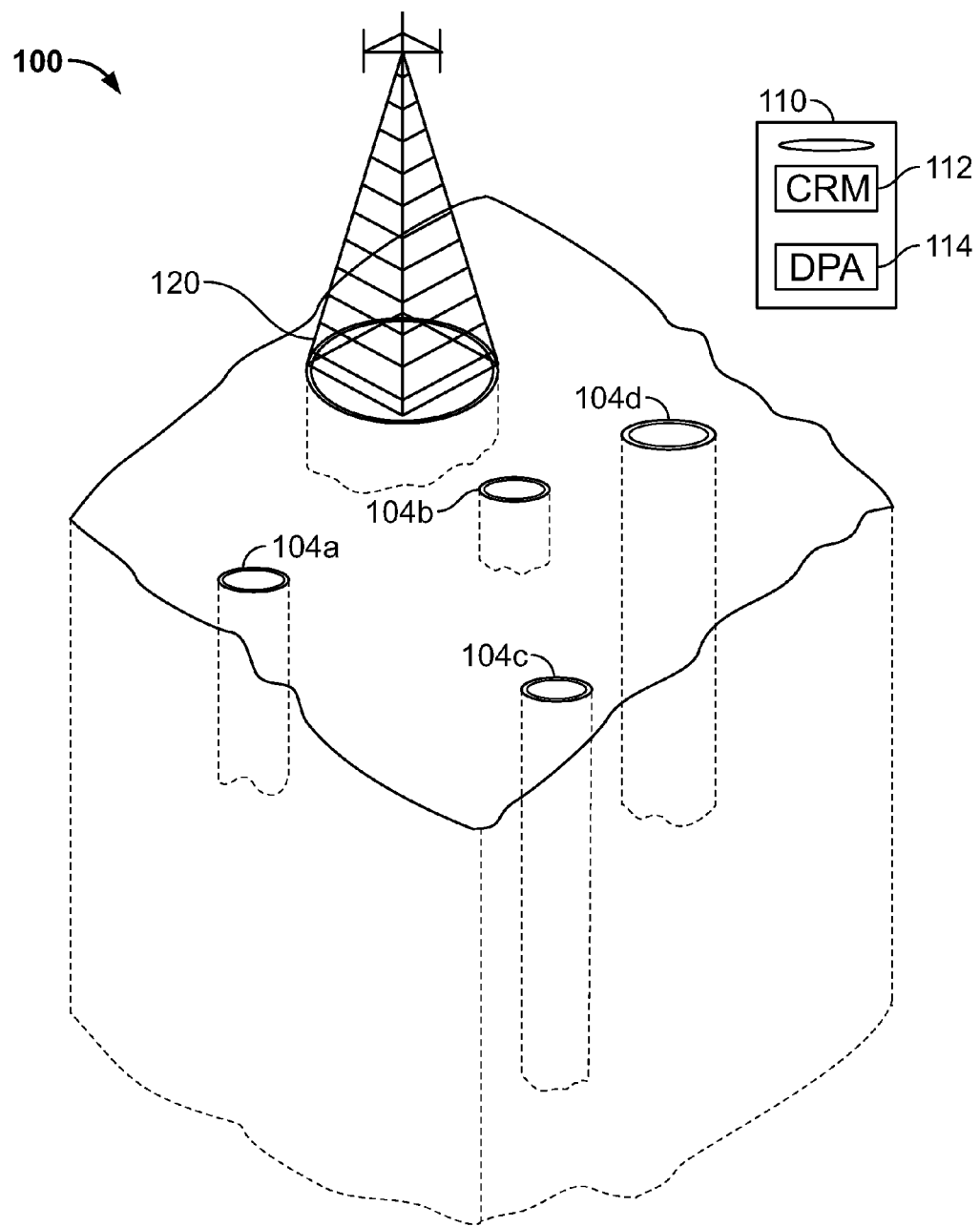
FIG. 1 is an example of a field from which multiple samples of oil are collected to develop a relationship between oil viscosities and biodegradation.

FIG. 1 is an example of a field 100 from which multiple samples of oil are collected to develop a relationship between oil viscosities and biodegradation. A field can include a geographical area that spans a length, a breadth, and a depth of a given zone of interest. Alternatively, or in addition, a field can include a portion of the geographical area or multiple geographical areas. To determine the suitability of the field 100 to produce oil and to identify one or more locations in the field 100 from which oil can be produced, the viscosities of oil at different locations in the field 100 can be used. In some implementations, multiple samples of oil (for example, oil from cuttings, oil from core samples, and the like) can be obtained from respective multiple locations (for example, locations 104a, 104b, 104c, and 104d) in the field 100. Oil samples can also be obtained from existing or concurrently drilled wells, such as well 120, in the field 100. For example, the location in which the well 120 is drilled may previously have been near a location from which oil was obtained.

Initially, oil can be obtained from multiple locations (locations 104a-d), for example, each at a respective depth. Using laboratory techniques, oil viscosities and amounts of bacteria in the multiple samples obtained from the multiple locations can be determined. In some implementations, the oil viscosities and amounts of bacteria can be stored, for example, on a computer system 110. From the oil viscosities and the amounts of bacteria in the multiple samples obtained from the multiple locations, a relationship that links oil viscosity to an amount of bacteria can be developed. In some implementations, the computer system 110 can execute computer instructions to determine an empirical relationship between oil viscosity and the amount of bacteria. Alternatively, or in addition, the empirical relationship can be developed manually and stored on the computer system 110.

Subsequently, oil can be obtained from one or more depths at each of multiple additional locations in the field 100. Amounts of bacteria in the oil obtained at each depth at each additional location can be determined using on-site techniques described below. Rather than implementing laboratory techniques to determine the oil viscosity of the oil obtained at each additional location, the viscosity can be determined by evaluating the chemistry of the oil using surface or downhole techniques to determine amount of bacteria in the oil. Then, the viscosity of the oil can be determined by comparing an amount of bacteria determined for oil obtained at each depth with the previously developed relationship. In this manner, the relationship can be used to determine a range of oil viscosities across different depths at different locations for the field 100.

The process of implementing on-site techniques to determine amounts of bacteria in core samples and cuttings, and using the relationship to determine the oil viscosities can be repeated at multiple locations in the field 100 (and also across multiple fields). In certain instances, the viscosity map can be developed while the field is either undeveloped with no wells or partially developed with a few wells. From the resulting ranges of oil viscosities, a viscosity map that represents oil viscosities of oil across zones in the fields can be developed. In sum, viscosity variation of oil across a field or across different fields can be mapped by linking biodegradation (i.e., bacteria activity) that affects oil formation in those areas to oil viscosities.

Implementing the techniques described here can offer one or more of the following potential advantages. Relative to NMR techniques, the techniques described here are unaffected by presence of fluids other than the oil, for example, capillary bound and clay bound water, in the formation. The techniques are also unaffected by the restricted diffusion, which can be difficult to correct, or by rock wettability. Whereas NMR techniques cannot be used to measure heavy oils with viscosities, particularly at shallow depths, due to the fast relaxation which is beyond the sensitivity of certain NMR laboratory tools, the techniques described here can be used to measure oil viscosities at shallow depths. The relationship between oil viscosity and biodegradation can be easier and cheaper to develop relative to models that relate oil viscosity and magnetic resonance measureable using NMR techniques. Moreover, the relationship between the oil viscosity and biodegradation in a zone need be developed only once and is subsequently continuously available for use across the field.

After initially using laboratory techniques to analyze the oil viscosities of and amounts of bacteria in a statistically significant number of samples (i.e., core samples or cuttings or combinations of them) and developing the relationship relating amounts of bacteria and oil viscosities, subsequent analysis can be implemented using on-site techniques thereby decreasing or eliminating laboratory analysis to determine oil viscosities. Moreover, the relationship can be refined over time by adding more data points, each data point obtained by analyzing an additional sample of oil at a location in the field. Similarly, each oil sample obtained from each well in any field can be used to continuously refine and update the viscosity map. In addition, the techniques can be independent of lithology, wettability, fluid effects, and borehole effects on logs (for example, salinity). The mapping techniques described here can also be extended to other components found in oil wells, for example, tar and asphaltene.

Figure 2:
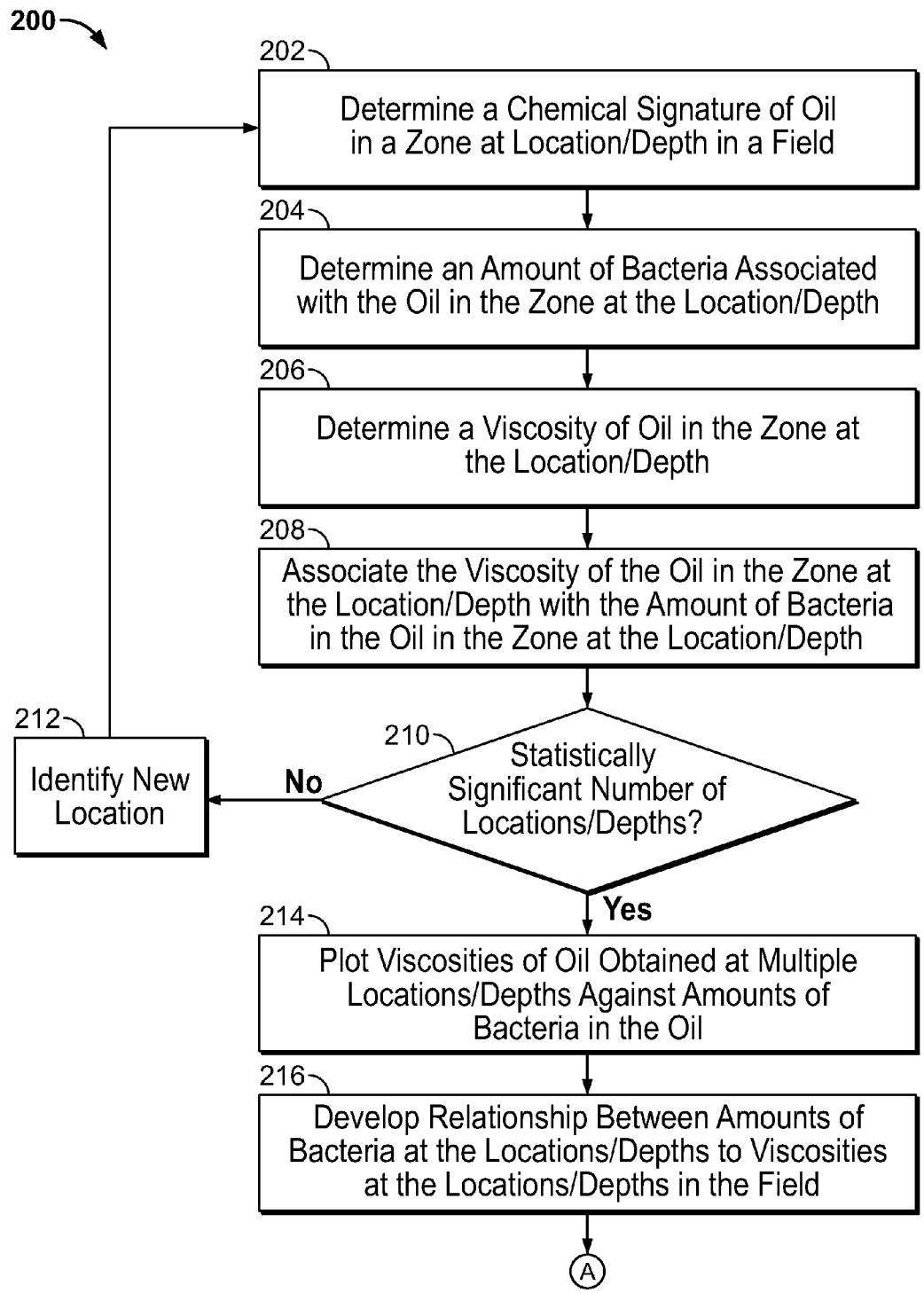
FIG. 2 is a flowchart of an example process for developing an oil viscosity map based on biodegradation.
Figure 2:
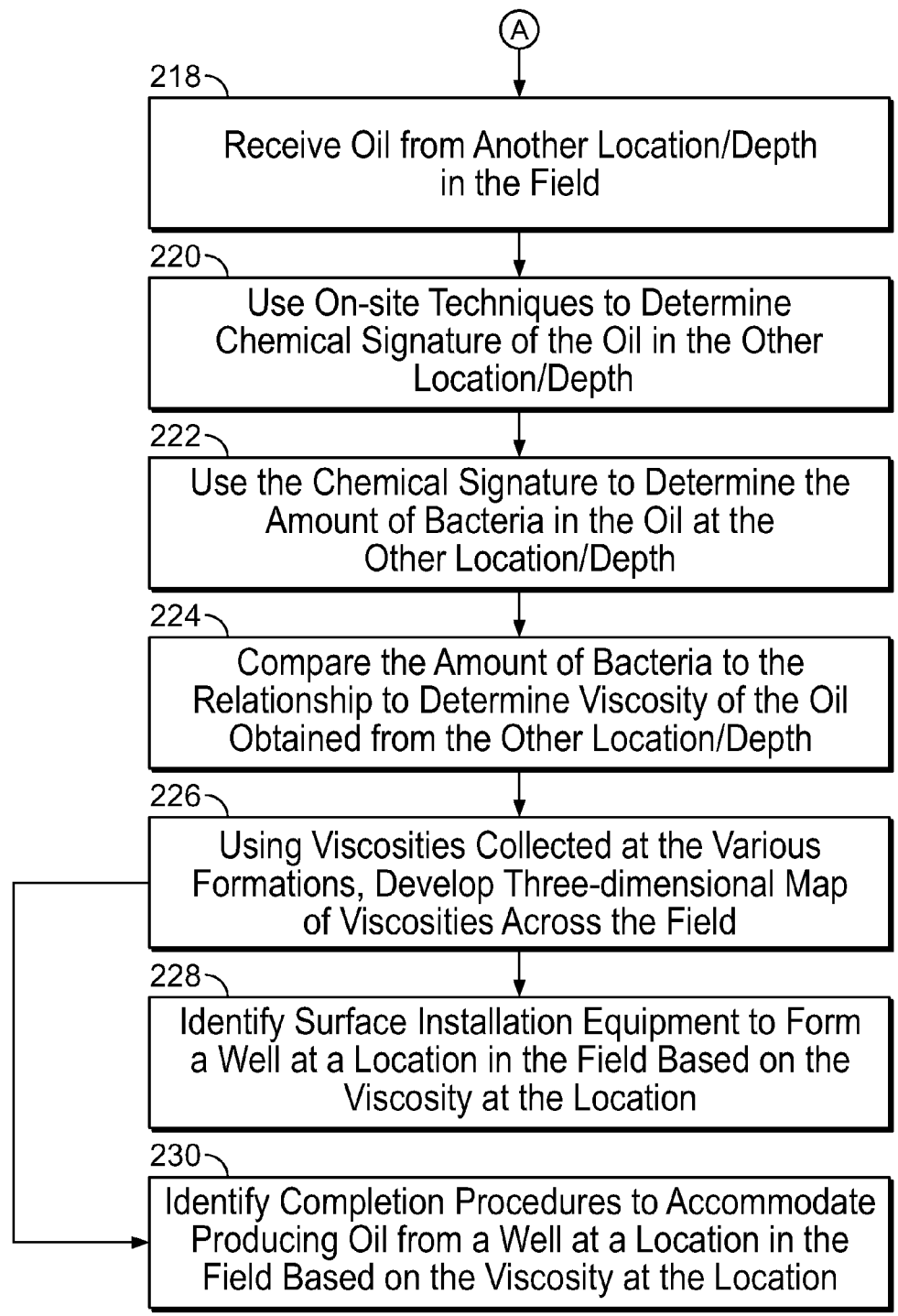

FIG. 2 is a flowchart of an example process 200 for developing an oil viscosity map based on biodegradation. The process 200 can be implemented to determine viscosity of oil in a subterranean zone, for example, at the locations 104a-d. The process 200 can include multiple steps (each described below), the first few of which (for example, steps 202, 204, 206, and 208) can be implemented to generate a relationship relating oil viscosities of oil at multiple locations to amounts of bacteria in the oil. At 202, a chemical signature of oil in the zone obtained at a location at a depth can be determined. In some implementations, the oil can be obtained from cuttings obtained from drilling a well or from a core sample of rock obtained from the zone at the location at the depth. Using laboratory techniques, (for example, elemental capture spectroscopy, X-Ray fluorescence spectroscopy, laser stratigraphy, pyrolysis, and the like), the chemical signature of the oil can be determined by determining an amount of one or more chemicals in the oil. The one or more chemicals can include at least one of vanadium, iron, nickel, or sulfur.

At 204, an amount of bacteria associated with the oil obtained at the location at the depth can be determined based on the chemical signature of the oil. For example, using laboratory techniques, the amounts of the chemicals (i.e., vanadium, iron, nick, or sulfur) can be determined and used as markers that uniquely identify the amount of bacteria in the oil. At 206, laboratory techniques can be used to determine a viscosity of oil obtained at the location at the depth. At 208, the viscosity of the oil determined at 206 can be associated with the amount of bacteria in the oil determined at 204. The amount of bacteria related to the viscosity can be the first data point of the relationship between viscosity and biodegradation.

The steps 202, 204, 206, and 208 can be repeated for multiple oil samples, each obtained at a different respective location and/or a different respective depth in the zone, until data points from a statistically significant number of locations/depths have been obtained. At 210, a check can be performed to determine if viscosities and amounts of bacteria at a statistically significant number of locations/depths have been determined. While core samples or cuttings (or combinations of them) may be obtained from a minimum number of samples to be statistically significant, samples can be obtained from more than a minimum number of statistically significant locations/depths to improve an accuracy of the relationship. If amounts of bacteria and viscosities have not been obtained from a statistically significant number of locations/depths (decision branch "NO"), then a new location/depth can be identified at 212, the steps 202, 206, 206, and 208 can be repeated.

If, on the other hand, amounts of bacteria and viscosities have been obtained from a statistically significant number of locations/depths (decision branch "YES"), then the viscosities of oil obtained at the multiple locations/depths can be plotted against the amounts of bacteria in the oil at 214 to generate a plot. From the plot, a lab-based relationship between amounts of bacteria at the locations/depths to viscosities at the locations/depths in the field can be developed at 216. The relationship can be an empirical relationship that relates oil viscosities to amounts of bacteria and represents a field-specific bacteria finger print for the entire field 100. Alternatively, or in addition, the plot can be mapped to a mathematical model into which amounts of bacteria can be provided as input and oil viscosity can be obtained as output. In some implementations, the data points and the empirical relationship or the plot (or both) can be stored, for example, in the computer system 110. As described below, the empirical relationship can subsequently be used to determine oil viscosity of oil obtained at subsequent locations/depths without requiring that the oil be transported to a laboratory for analysis.

In some implementations, after the relationship has been developed, oil can be obtained from multiple other locations formed in the field at a different depth in each location to further determine a viscosity profile of the field 100. At 218, oil can be received from a location/depth in the field 100. For example, the other location/depth can be one of the locations 104a-d but at a different depth or a location/depth other than the locations 104a-d. The oil can be obtained from additional core samples or from existing core samples or from concurrently drilled wells (for example, wells drilled in development of the field) or combinations of them. For oil obtained at each other location/depth, down-hole or surface on-site techniques can be used to determine a respective chemical signature of the oil at 222. For example, the chemical signature can be determined by at least one of neutron-induced capture gamma ray spectroscopy, laser-induced fluorescence spectroscopy, or pyrolysis (or by combinations of them) or the like. The neutron-induced capture gamma ray spectroscopy can be implemented, for example, using a down hole tool such as the GEM™ Elemental Analysis Tool (provided by Halliburton, Inc., Houston, Tex.). The laser-induced fluorescence spectroscopy can be implemented, for example, using a surface tool such as the LaserStrat® Wellsite Chemostratigraphy Service (provided by Halliburton, Inc., Houston, Tex.) to analyze drilling cuttings.

At 224, the chemical signature can be used to determine the amount of bacteria in the zone at the other location. The chemical signatures represent bacteria finger prints that can be used to establish a distribution of bacteria amounts at different depths in the multiple locations across the field 100. The amount of bacteria can be compared to the relationship to determine and provide viscosity of the oil obtained from the other location at 224.

By repeatedly implementing process 200 for multiple locations/depths, variations of viscosities across the field can be obtained. From these viscosities, a three-dimensional map of viscosities can be generated, and, in some implementations, stored in the computer system 110. The three-dimensional map can be used to develop a field development plan to extract oil from across the field 100, which, in turn, can affect decisions on the production economics in the area.

At 228, one or more surface installation equipment to form a producing well at a location can be identified based on the viscosity at the location. For example, equipment such as valves, chokes, pumps, and other provisions for injection (such as, steam, chemicals, water, and the like), that are needed to extract oil from the producing well can be identified. Because the oil viscosities drive the choice of such equipment, knowing the oil viscosity can enable selection of appropriate equipment. Alternatively, or in addition, at 230, well configuration and completion procedures to accommodate producing oil from the well—such procedures depending on the identified oil viscosities—can also be identified. For example, a zone can include low viscosity oil that can flow without assistance until a certain depth and high viscosity oil that cannot flow without assistance beyond that depth. The low viscosity oil may be extractable without assistance whereas the high viscosity oil may need assistance, such as steam enhanced recovery techniques, to be extracted. Knowing the viscosity of the oil at various depths in the zone can enable determining a type of assistance that may be needed to produce oil from the well and also to determine when such assistance may need to be implemented. The information describing the viscosity can also be used to select locations for drilling wells and also to select a number of wells that can be drilled at each location.

Figure 3:
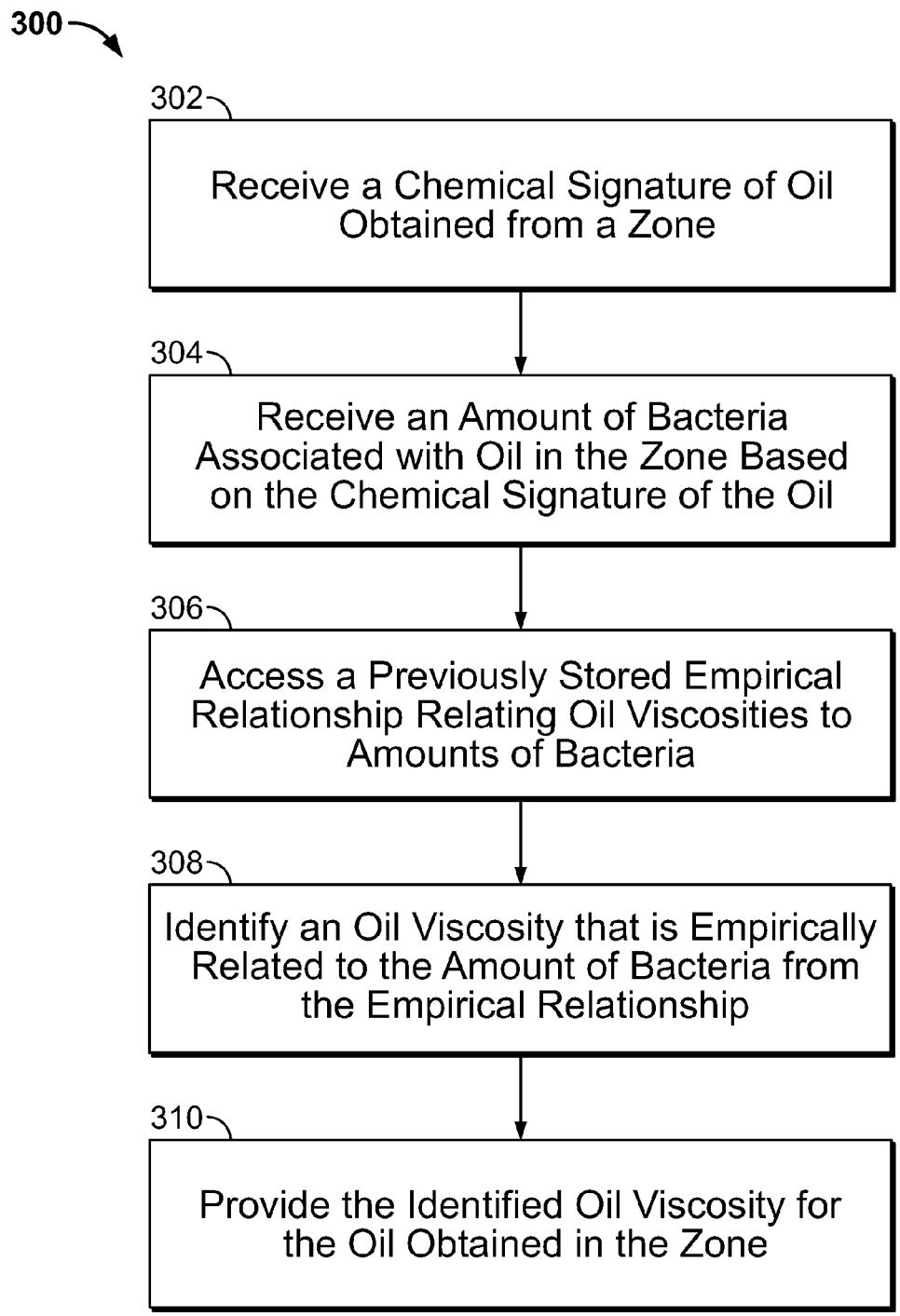
FIG. 3 is a flowchart of an example process implemented by a computer system for determining oil viscosity based on a relationship between oil viscosities and amounts of bacteria in oil.

FIG. 3 is a flowchart of an example process 300 implemented by a computer system, for example, computer system 110, for determining oil viscosity based on a relationship between oil viscosities and amounts of bacteria in oil. At 302, the computer system 110 receives a chemical signature of oil obtained from a zone, and at 304, receives an amount of bacteria associated with oil in the zone based on the chemical signature of the oil. At 306, the computer system 110 accesses a previously stored empirical relationship relating oil viscosities to amounts of bacteria. The computer system 110 can determine the empirical relationship, for example, by implementing steps of process 200 described above, and store the relationship, for example, in the computer-readable medium 112. At 308, the computer system 110 can identify an oil viscosity that is empirically related to the amount of bacteria from the empirical relationship. At 310, the computer system 110 can provide the identified oil viscosity for the oil obtained in the zone. For example, the computer system 110 can display the empirical relationship or the oil viscosity (or both) in a display device connected to the computer system 110. The computer system 110 can also compile the three dimensional-map of viscosities from the multiple data points. In some implementations, the computer system can control the three-dimensional map if an attribute can be linked to amount of bacteria or chemical signature (or both). For example, the amount of bacteria, chemical signature, or both can be linked to seismic attribute or borehole seismic (or both) to restrain and better control the oil viscosity map between wells. The seismic information can be used to guide propagation of oil viscosity mapping (variation) between wells where no information or measurement is available.

Figure 4:
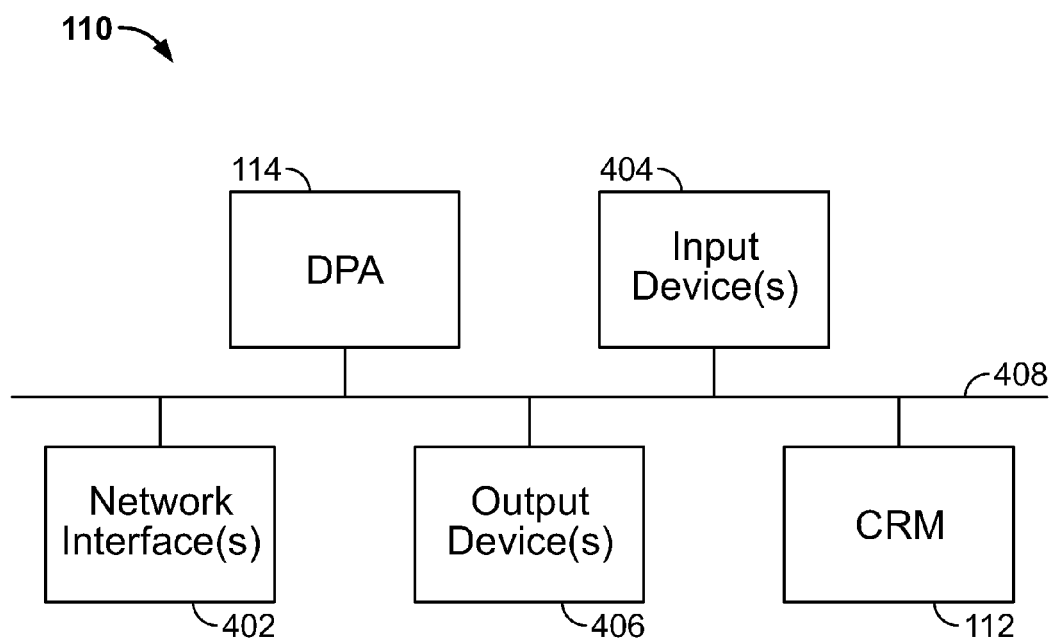
FIG. 4 is an example of an architecture of the computer system of FIG. 3.

FIG. 4 is an example of an architecture of the computer system of FIG. 3. The computer system includes one or more data processing apparatus 114 and a computer-readable medium 112 storing computer instructions executable by the one or more data processing apparatus 114 to determine viscosity of oil in a well. The computer system can be a desktop computer, a laptop computer, a personal digital assistant (PDA), a smartphone, a table computer, and the like. The computer system can include one or more network interfaces 402 and one or more input devices 404, for example, a keyboard, a touch screen, mouse, trackball, track pad, and the like. The computer system can also include one or more output devices 406, for example, display devices that implement Liquid Crystal Display (LCD) or Light Emitting Diode (LED) technology, printers, data transmission equipment, and the like. The components of the computer system can be coupled by a bus 408.

A number of embodiments have been described. Nevertheless, it will be understood that various modifications may be made without departing from the spirit and scope of the invention. For example, because the oil viscosity is related to biodegradation, it can first be determined that biodegradation is the dominant cause of oil formation in the zones across the field. Biodegradation dominates other causes of oil formation in shallow wells.

What is claimed is:

1. A method to determine viscosity of oil in a subterranean zone of interest, the method comprising:
   obtaining the oil from cuttings from drilling the zone or from a core sample of rock obtained when drilling the zone;
   determining a chemical signature of the oil in the zone;
   determining an amount of bacteria associated with the oil based on the chemical signature of the oil;
   identifying, from a relationship relating oil viscosities to amounts of bacteria, an oil viscosity for the amount of bacteria; and
   providing the oil viscosity for the oil.

2. The method of claim 1, further comprising determining the chemical signature by at least one of neutron-induced capture gamma ray spectroscopy, laser-induced fluorescence spectroscopy, or pyrolysis.

3. The method of claim 1, wherein the relationship is an empirical relationship, and wherein the method further comprises determining the empirical relationship relating oil viscosities to amounts of bacteria by:
   obtaining oil from a plurality of locations formed in a field at a respective depth in each location;
   for oil obtained at each location at the respective depth:
      determining an amount of bacteria in the oil based on a respective chemical signature of the oil,
      determining a viscosity of the oil, and
      associating the viscosity of the oil with the amount of bacteria in the oil; and
   developing a relationship between viscosities of the oil and amounts of bacteria in the oil.

4. The method of claim 3, wherein developing the relationship between viscosities of the oil and amounts of bacteria in the oil comprises:
   plotting the viscosities of the plurality of oil samples against the amounts of bacteria in the plurality of oil samples to generate a plot of the empirical relationship; and
   storing the plot.

5. The method of claim 1, wherein determining the chemical signature of the oil comprises determining an amount of one or more chemicals in the oil.

6. The method of claim 5, wherein the one or more chemicals includes at least one of vanadium, iron, nickel, or sulfur.

7. The method of claim 1, further comprising identifying oil viscosities for oil obtained at a respective plurality of depths in the zone.

8. The method of claim 7, further comprising identifying one or more surface installation equipment to form a producing oil well at the field based on the identified oil viscosities.

9. The method of claim 7 further comprising identifying completion procedures to accommodate producing oil from the zone, wherein the completion procedures are based on the identified oil viscosities.

10. The method of claim 7, further comprising generating a three-dimensional map of viscosities based on the identified oil viscosities.

11. A method to determine viscosity of oil in a subterranean zone, the method comprising:
   generating a relationship relating oil viscosities of oil from a plurality of samples from the zone to amounts of bacteria in the oil;
   receiving oil obtained from the zone;
   determining an amount of bacteria in the received oil from a chemical signature of the received oil;
   identifying an oil viscosity of the received oil from the relationship; and
   providing the oil viscosity for the received oil.

12. The method of claim 11, further comprising determining the chemical signature by at least one of neutron-induced capture gamma ray spectroscopy, laser-induced fluorescence spectroscopy, or pyrolysis.

13. The method of claim 11, wherein the relationship is an empirical relationship, and wherein generating the empirical relationship comprises:
   obtaining oil from cuttings or from core samples of rocks obtained from the zone at a plurality of locations at a respective depth in each location; and
   for oil obtained at each location at a respective depth:
      determining an amount of bacteria in the oil based on a chemical signature of the oil,
      determining a viscosity of the oil, and
      associating the viscosity of the oil with the amount of bacteria in the oil.

14. The method of claim 11, further comprising:
   identifying one or more surface installation equipment to form a producing oil well at the field based on the identified oil viscosity; and
   identifying completion procedures to accommodate producing oil from the producing oil well, wherein the completion procedures are based on the identified oil viscosity.

15. The method of claim 11, wherein determining the chemical signature of the received oil comprises determining an amount of one or more chemicals in the received oil.

16. The method of claim 15, wherein the one or more chemicals includes at least one of vanadium, iron, nickel, or sulfur.

17. A computer system comprising:
   one or more data processing apparatus; and
   a computer-readable medium storing computer instructions executable by the one or more data processing apparatus to determine viscosity of oil in a subterranean zone, the operations comprising:
      receiving a chemical signature of oil obtained from the zone;
      receiving an amount of bacteria associated with oil in the zone based on the chemical signature of the oil;
      accessing an empirical relationship relating oil viscosities to amounts of bacteria, wherein determining the empirical relationship relating oil viscosities to amounts of bacteria by:
         obtaining oil from cuttings or from core samples of rocks obtained from the zone at a plurality of locations at a respective depth in each location; and
         for oil obtained at each location at a respective depth:
            determining an amount of bacteria in the oil based on a chemical signature of the oil,
            determining a viscosity of the oil, and
            associating the viscosity of the oil with the amount of bacteria in the oil; and
         developing a relationship between viscosities of the plurality of oil samples and amounts of bacteria in the plurality of oil samples;
      identifying, from the empirical relationship, an oil viscosity that is empirically related to the amount of bacteria; and
      providing the identified oil viscosity for the oil obtained in the zone.

18. The computer system of claim 17, further comprising a computer-readable storage medium storing the empirical relationship and a three-dimensional map of viscosities generated based on the identified oil viscosities.

19. The computer system of claim 18, wherein the operations further include controlling a mapping of viscosities if an attribute is linkable to an amount of bacteria or chemical signature.

* * * * *